US010208132B2

(12) United States Patent
King et al.

(10) Patent No.: US 10,208,132 B2
(45) Date of Patent: Feb. 19, 2019

(54) METHOD OF MODIFYING POLYMERS

(71) Applicants: Metsä Fibre Oy, Metsä (FI); Stora Enso Oyj, Helsinki (FI)

(72) Inventors: Alistair W. T. King, University of Helsinki (FI); Christoph Selg, University of Helsinki (FI); Pirkko Karhunen, University of Helsinki (FI); Jorma Matikainen, University of Helsinki (FI); Ilkka Kilpeläinen, University of Helsinki (FI)

(73) Assignees: Metsa Fibre Oy, Metsa (FI); Stora Enso Oyj, Helsinki (FI)

( * ) Notice: Subject to any disclaimer, the term of this patent is extended or adjusted under 35 U.S.C. 154(b) by 35 days.

(21) Appl. No.: 14/893,751

(22) PCT Filed: May 26, 2014

(86) PCT No.: PCT/FI2014/050412
§ 371 (c)(1),
(2) Date: Nov. 24, 2015

(87) PCT Pub. No.: WO2014/188081
PCT Pub. Date: Nov. 27, 2014

(65) Prior Publication Data
US 2016/0145356 A1 May 26, 2016

(30) Foreign Application Priority Data
May 24, 2013 (FI) .................................... 20135569

(51) Int. Cl.
C08B 37/08 (2006.01)
C08B 11/00 (2006.01)
(Continued)

(52) U.S. Cl.
CPC .......... *C08B 37/003* (2013.01); *C07K 14/415* (2013.01); *C08B 5/00* (2013.01);
(Continued)

(58) Field of Classification Search
CPC ........................... C07K 14/415; C08B 37/003
See application file for complete search history.

(56) References Cited

U.S. PATENT DOCUMENTS 3,553,194 A 1/1971 Verbanac et al.
4,150,021 A 4/1979 Swidler et al.
(Continued)

FOREIGN PATENT DOCUMENTS

CN 101160325 A 4/2008
CN 101395184 A 3/2009
(Continued)

OTHER PUBLICATIONS

International Search Report for PCT/FI2014/050412 dated Aug. 19, 2014.
(Continued)

*Primary Examiner* — Melvin C. Mayes
*Assistant Examiner* — Stefanie J Cohen
(74) *Attorney, Agent, or Firm* — McCormick, Paulding & Huber LLP

(57) ABSTRACT

A method of modifying a polymer having hydroxyl groups, selected from the group of polysaccharides and lignin, to give a modified polymer comprising the step of contacting said polymer with at least one organic phosphonate salt in order to chemically modify the polymer, said organic phosphonate salt being in a liquid phase. The method of polymer modification provides novel polymers. Modified polymers obtained from a polymer having been treated with at least one organic phosphonate salt are also disclosed. The modified polymers can be used as such or separated and optionally recovered from the solution, optionally being formed into particular materials or shapes.

21 Claims, 2 Drawing Sheets

IR-spectra of (top to bottom) Bahia pulp, phosphorylated bahia pulp from reactive dissolution at 130 °C as powder and thinfilm, at 130 °C and at 70 °C with catalyst DBU.

(51) Int. Cl.

| | | |
|---|---|---|
| *C07K 14/415* | (2006.01) | |
| *C08B 5/00* | (2006.01) | |
| *C08L 1/02* | (2006.01) | |
| *C08L 5/08* | (2006.01) | |
| *C08L 97/02* | (2006.01) | |
| *D01F 2/28* | (2006.01) | |

(52) U.S. Cl.
CPC ............... *C08B 11/00* (2013.01); *C08L 1/02* (2013.01); *C08L 5/08* (2013.01); *C08L 97/02* (2013.01); *D01F 2/28* (2013.01)

(56) References Cited

U.S. PATENT DOCUMENTS

| | | |
|---|---|---|
| 4,358,587 A | 11/1982 | Brandt et al. |
| 6,508,958 B1 | 1/2003 | Wojcik |
| 2010/0121075 A1 | 5/2010 | Nguyen et al. |
| 2011/0196139 A1 | 8/2011 | Lee et al. |

FOREIGN PATENT DOCUMENTS

| | | |
|---|---|---|
| CN | 101400704 A | 4/2009 |
| CN | 102311554 A | 1/2012 |
| SU | 912729 A1 | 3/1982 |

OTHER PUBLICATIONS

Finnish Search Report for FI Patent Appln. Serial No. 20135569 dated Feb. 17, 2014.

Heras A. et al, "N-methylene phosphonic chitosan: a novel soluble derivative", Carbohydrate Polymers, Applied Science Publishers, Ltd., Barking, GB, vol. 44, No. 1, Jan. 1, 2001, pp. 1-8.

Huyen Thanh Vo et al, "Ionic-Liquid-Derived, Water-Soluble Ionic Cellulose", Weinheim an der Bergstrasse, Germany, Jul. 16, 2012, pp. 9019-9023.

Xie Haibo et al, "Opportunities with Wood Dissolved in Ionic Liquids" in Tim F. Liebert, Thomas J. Heinze, Kevin J. Edgar (ed.) Cellulose Solvents: For Analysis, Shaping and Chemical Modification ACS Symposium Series, vol. 1033, 2010, pp. 343-363.

Mantz Robert A. et al, "Dissolution of Biopolymers Using Ionic Liquids", Z. Naturforsch. 62a, 2007, pp. 275-280.

Chinese Search Report for Serial No. 201480041629.9 dated Feb. 4, 2017.

METHOD OF MODIFYING POLYMERS

CROSS REFERENCE TO RELATED APPLICATIONS

This application is entitled to the benefit of and incorporates by reference subject matter disclosed in International Patent Application No. PCT/FI2014/050412 filed on May 26, 2014 and Finnish Patent Application No. 20135569 filed May 24, 2013.

TECHNICAL FIELD

The present invention relates to a method of modifying a polymer having hydroxyl groups. In such a method an organic phosphonate salt in a liquid phase is applied to the polymer in order to chemically modify the polymer. The present invention also relates to a modified polymer. Further, the invention relates to a solution containing the modified polymer.

BACKGROUND ART

Polymers have been provided by nature in abundance and in a range of forms from biopolymers including polysaccharides such as cellulose to proteins such as collagen, each biopolymer able to undergo processes according to its own properties.

There are a number of methods in the art for modifying biopolymers, these include e.g. introduction of an aldehyde group into a protein, peptide or oligo through an amine reactive agent, or through diol oxidation, introduction of sulfhydryl groups through disulfide bond reduction and introduction of thiol groups by amine modification. Modifications involving the formation of ether groups are disclosed in U.S. Pat. Nos. 3,553,194 and 4,358,587. A treatment of viscose is disclosed in the Soviet publication SU 912,729, the formation of amide bonds is disclosed in U.S. Pat. No. 6,508,958 and a modified starch is disclosed in Chinese publication CN 102,311,554.

Many of these biopolymers are scarcely soluble in traditional molecular solvents such as apolar or polar organic solvents and thus modification is difficult and carried out under extreme conditions aided by prohibitively expensive and often toxic catalysts, such as cobalt, chromium, cerium, mercury, nickel and tin, which are all elements of high concern. However, it has recently been shown that lignocelluloses can be successfully dissolved in ionic liquids, cf. Haibo Xie, Ilkka Kilpeläinen, Alistair King, Timo Leskinen, Paula Järvi, and Dimitris S. Argyropoulos, "Opportunities with Wood Dissolved in Ionic Liquids" in Tim F. Liebert, Thomas J. Heinze, Kevin J. Edgar (ed.) *Cellulose Solvents: For Analysis, Shaping and Chemical Modification* ACS Symposium Series, Volume 1033 (2010), p. 343-363.

SUMMARY OF INVENTION

It has been found that the harsh conditions under which chemical modification of polymers takes place and the toxicity and environmental threats, as well as the added expense of catalysts, make satisfactory polymer modification problematic. Cellulose, as a hydroxylated polymer, is particularly difficult to process due to its crystalline nature and H-bonded network. For dissolution and chemical modification of cellulose, expensive solvents and more complex chemicals are often used, which prevents recyclability and process scale-up.

It is an aim of the present invention to eliminate at least part of the problems related to the known methods and to provide a method of modifying a polymer under moderate conditions and without the need for toxic and expensive catalysts It is a further aim of the invention to provide modified polymers. An additional aim of the invention is to provide uses of the modified polymers. A particular aim of the invention is to provide a solution containing a modified polymer.

The invention is based on the concept of contacting polymers containing hydroxyl groups with organic compounds containing phosphonate groups in liquid phase in order to modify the polymers. Typically, the organic phosphonate compounds are employed in the form of organic phosphonate salts.

It has been found that hydroxyl groups present in the polymers are capable of reacting with phosphonate groups to give polymer phosphonates. A treatment of this kind provides an at least partial phosphonylation of the polymer providing polymer phosphonates.

The modified polymers are, potentially, at least partially soluble in simple liquids, such as water or other polar solvents, or mixtures thereof.

By contacting polymers containing hydroxyl groups with organic phosphonates in liquid phase, solutions of modified polymers can be provided.

The modified polymers can be used as such or separated and optionally recovered from the solution, optionally being formed into particular materials or shapes.

Thus, the polymer can be provided in the form of fibres or filaments. The polymer can also be used for producing spun fibres and thin films.

The properties of such functionalised polymers including flame retardancy, adsorptivity, absorptivity, flocculation ability and conductivity, can be varied by the choice of polymer, the choice of organic phosphonate and the degree and selectivity of the reaction. Thin films manufactured from the present polymers exert, for example, oxygen barrier properties.

Polymers suitable for undergoing treatment with organic phosphonate salts include but are not limited to biopolymers containing hydroxyl groups, e.g. polymers selected from the group of polysaccharides, such as cellulose, hemicelluloses, starch and other biopolymers, such as lignin, chitin and chitosan. Other synthetic hydroxylated polymers may be used, such as polyvinyl alcohol (PVA) or polylactic acid (PLA).

More specifically the method according to the present invention is characterized by a method of modifying a polymer having hydroxyl groups to give a modified polymer comprising the step of contacting said polymer with at least one organic phosphonate salt in order to chemically modify the polymer, said organic phosphonate salt being in a liquid phase, and wherein the organic phosphonate salts are of Formula III

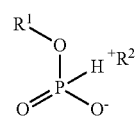

III wherein
$R^1$ is selected from a hydrogen radical, a linear or branched alkyl radical having 1 to 20 carbon atoms, an aryl radical having 4 to 24 carbon atoms, and $R^2$ is a cation selected from the group of $H^+$, $Li^+$, $Na^+$, $K^+$, $Rb^+$, $Cs^+$, $Fr^+$, $Cu^+$, $Ag^+$, substituted and unsubstituted ammonium, phosphonium, and sulfonium, and five-membered heterocycles having 1,2 and 3 heteroatoms and mixtures thereof.

The modified polymers according to the present invention are characterized by a polymer obtained by a method. The solution according to the present invention is defined in claim 31 by comprising a polymer dissolved or dispersed in a liquid phase.

Considerable benefits are gained with the aid of the invention. The present simple, easy to conduct method of polymer modification under moderate conditions provides novel polymers.

Other features and advantages will become apparent from the following description.

BRIEF DESCRIPTION OF DRAWINGS

Next the invention will be examined more closely with the aid of a detailed description and with reference to the attached drawings, in which.

DETAILED DESCRIPTION

Figure 1:
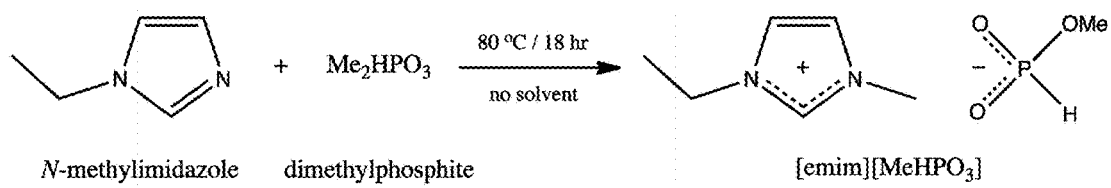
FIG. 1 shows a potential reaction mechanism for the synthesis of [emim][MeHPO$_3$]

As discussed above, the present technology provides for dissolution of polymers having hydroxyl groups in liquid phase by modification, in particular chemical modification, of the polymers. The modification involves a step of contacting the polymers in liquid phase with organic phosphonates or organic phosphonate compounds that preferably are provided in the form of salts.

Without wishing to be limited to any particular reaction mechanism, the following reaction scheme II is given for illustrative purposes (as apparent, the phosphonate anion is countered by an organic or inorganic cation):

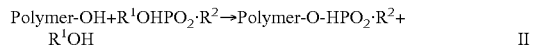

$R^1$ stands for H or an organic residue, such as an alkyl or aryl radical
$R^2$ represents an organic or inorganic cation The invention relates to a method of modifying a polymer having hydroxyl groups, selected from the group of polysaccharides and lignin, to give a modified polymer comprising the step of contacting said polymer with at least one organic phosphonate salt in order to chemically modify the polymer, said organic phosphonate salt being in a liquid phase. The method of polymer modification provides novel polymers. Modified polymers obtained from a polymer having been treated with at least one organic phosphonate salt are also disclosed. The modified polymers can be used as such or separated and optionally recovered from the solution, optionally being formed into particular materials or shapes.

By means of the present method, a phosphonylation product can be formed from the polymer, said polymer product containing phosphonylated groups derived from a chemical reaction between the organic phosphonate salt and hydroxyl groups present in the constituent molecules of the polymer.

One embodiment concerns a method of modifying a polymer having hydroxyl groups, comprises the step of contacting said polymer with at least one organic phosphonate salt in order to chemically modify the polymer, said organic phosphonate salt being in a liquid phase.

In a further embodiment the polymer is reacted with the organic phosphonate salt to form a chemical derivative of the polymer.

In one embodiment the polymer to be modified is contacted with organic phosphonate salts having Formula III

that is equal to

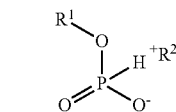

wherein
$R^1$ is a hydrogen radical, a linear or branched alkyl radical having 1 to 20 carbon atoms, preferably 1 to 15 carbon atoms, particularly 1 to 10 carbon atoms, advantageously 1 to 5 carbon atoms, or an aryl radical having 4 to 24 carbon atoms, in particular 5 to 18 carbon atoms, said aryl radical optionally comprising at least one heteroatom selected from O, N and S, said alkyl and said aryl radical optionally being substituted with 1 to 10 substituents selected from hydroxyl, carboxy, halo, amino, and thio groups, and
$R^2$ stands for a cation selected from the group of $NH_4^+$, $H^+$, $Li^+$, $Na^+$, $K^+$, $Rb^+$, $Cs^+$, $Fr^+$, $Cu^+$, $Ag^+$, substituted and unsubstituted ammonium, phosphonium, and sulfonium, and five-membered heterocycles having 1,2 and 3 heteroatoms including but not limited to methyl-pyrrolidinium, isothiazolium, isoxazolium, oxazolium, pyrrolium, and thiophenium-pyridinium, pyridazinium, pyrimidinium, pyrazinium, imidazolium, pyrazolium, thiazolium, oxazolium, amidinium, guanidinium, phosphazenium, 1-ethyl-3-methylimidazolium, and triazolium, and mixtures thereof.

In a further embodiment $R^2$ is an ammonium or phosphonium ion substituted by one or more groups selected from the group of linear or branched alkyl radicals, said alkyl radicals having 1 to 10 carbon atoms, preferably 1 to 8 carbon atoms, advantageously 1 to 5 carbon atoms, most preferably 1 to 4 carbon atoms, or a mixture thereof, or an aryl radical having 4 to 24 carbon atoms, in particular 5 to 18 carbon atoms, said aryl radical optionally comprising at least one heteroatom selected from O, N and S, said alkyl and said aryl radical optionally being substituted with 1 to 10 substituents selected from hydroxyl, carboxy, halo, amino, and thio groups.

Naturally, mixtures of phosphonate salts can be used also. Such mixtures may contain organic phosphonate salt compounds, having two or more different cations of the above kind.

As used herein, the term "liquid phase" has a broad meaning and includes, but is not limited to, neat liquids of organic phosphonate salts as well as solutions and dispersions of the above-mentioned type of organic phosphonate salts in water and other solvents to provide electrolyte solutions.

Examples of solvents are polar solvents, alkanols typically having 1 to 6 carbon atoms, such as methanol, ethanol, n- and i-propanol and n-, i- and t-butanol, amyl alcohol and mixtures thereof, aromatic alcohols, such as phenol or benzalcohol, and mixtures thereof as well as mixtures of aliphatic and aromatic alcohols.

Examples of useful polar aprotic solvents are DMSO, DMA, DMF, dimethylcarbonate, propylene carbonate, TMU, DMPU, and mixtures thereof.

The term "liquid phase" also encompasses mixtures of neat liquids.

In one embodiment the amount of organic phosphonate salt in the liquid phase is between 0.1 and 100.0% of the total weight of the liquid phase.

In an embodiment, the concentration of the organic phosphonate salt is preferably between 1.0 and 50.0%, advantageously between 2.0 and 20.0% and particularly between 8.0 and 12.0% of the total weight of the liquid phase.

In a further embodiment the polymer is contacted with the phosphonate salt at a molar ratio of hydroxyl groups to phosphonate groups of 1:0.1 to 1:1000, in particular 1:0.5 to 1:100, for example 1:1 to 1:50. In a particular embodiment the polymer is modified by chemical reaction between the organic phosphonate salts and hydroxyl groups of the polymer, said chemical reaction giving polymer phosphonates and a weight percent gain (WPG) in the polymer of 0.001-1500%, preferably 1.000-1000%, advantageously 5.000-900%, particularly 10.000-700%.

The contacting can be carried out at ambient or increased pressure. The temperature is typically higher than ambient, i.e. higher than about 25° C. Preferably the temperature is lower than the decomposition point of the organic phosphonate salt. A suitable range is about 50 to about 250° C., for example about 60 to 200° C., such as 70 to 150° C.

The contacting can be enhanced by subjecting the components to mixing, preferably at turbulent conditions. The contacting time is typically 0.1 to 48 hours, in particular about 0.2 to 24 hours, for example about 0.5 to 15 hours, or 1 to 12 hours.

The reaction can be carried out in ambient atmosphere or in inert atmosphere, the latter being preferred.

The reaction can be carried out at atmospheric pressure or low pressure, to facilitate removal of by-products and shift reaction equilibria.

Catalysts can be employed, such as strong bases and/or amines, e.g. 1,1,3,3-tetramethyl-guanidine (TMG), 1,1,2,3,3-pentamethylguanidine (PMG) or 1,8-diazabicyclo[5.4.0]undec-7-ene (DBU), 1,5-Diazabicyclo[4.3.0]non-5-ene (DBN), Bartons base, or other common organic bases, such as pyridine, triethylamine or Hünigs base.

Further embodiments provide modified polymers. One such embodiment describes a polymer obtained by a method according to any of the preceding claims. A further embodiment discloses a polysaccharide or lignin polymer comprising phosphonate groups.

In a particular embodiment, the polymer further comprises hydroxyl groups, the ratio of phosphonate groups to hydroxyl groups being 1000:1 to 1:1000, in particular 100:1 to 1:100, for example about 10:1 to 1:10.

As a result of the contacting step a modified polymer is obtained which exhibits phosphonate groups. Preferably the polymer are derived from organic phosphonate salts of Formula III $$R^2 \cdot R^1\text{-OHPO}_2 \qquad \text{III}$$

that equals to

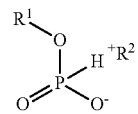

wherein $R^1$ and $R^2$ have the same meaning as above.

All of the above embodiments can be applied to polymers included in, but not limited to, the group of biopolymers, i.e. polymers derived from biological material. Such biopolymers are preferably selected from the group of polysaccharides, such as cellulose, hemicelluloses and starch, and other hydroxyl-biopolymers, such as lignin, chitin and chitosan, and from derivatives thereof, including but not limited to organic and inorganic cellulose esters, alkyl, hydroxyalkyl and carboxymethyl cellulose ethers, dextrins and trimethyl chitosans.

Cellulose can be formed by purified chemical material or it can comprise industrial cellulose sources, such as chemical, semichemical or mechanical pulps obtained by defibering lignocellulosic raw materials. Such raw materials are exemplified by annual and perennial plants, as well as wood of deciduous or coniferous species. Suitable wood species include, but are not limited to, spruce, pine, birch, poplar, aspen, and eucalyptus.

In one embodiment, chemical pulp used as a starting material is obtained from pulping at alkaline, acid or neutral conditions. Particularly suitable pulp is pulp obtained by pulping at alkaline conditions or by organic solvents (organosolv, milox etc.). As examples of sources of cellulose the following can be mentioned: pulp obtained by the kraft method, pulp obtained by the polysulphide method and pulp obtained by the soda method.

The pulp can be modified before the contacting step. Thus, in one embodiment the pulp is pre-hydrolysed, for example with alkali or acid. One example is pre-hydrolysis kraft pulp.

Based on the above, cellulosic pulps, such as chemical pulps and more specifically 'dissolving' pulps, produced by conventional pulping, for example by a kraft, pre-hydrolysis kraft (PHK), sulphite, soda, soda-anthroquinone (S-AQ), pre-hydrolysis soda, or S-AQ, or organosolv cooking processes, are particularly interesting raw-materials.

Hemicellulose may also be derived from wood, but also from any number of sources including but not limited to rice bran, rye bran, beet pulps, wheat bran, wheat straw, corn cobs, soya bean hulls, maize bran, oats husk, spelt wheat husk, grass hay and ground wheat. Lignin may be derived from the various sources of wood mentioned above.

In one embodiment, hemicellulose is obtained by extraction, for example, by extraction at alkaline conditions from industrial cellulose pulps.

Chitin, structurally similar to cellulose, comes from various sources. Sources in both the animal and fungi kingdoms are known, including but not limited to cell walls of fungi and exoskeletons of arthropods, such as crustaceans and insects. Chitosan is produced from the deacetylation of chitin obtained from any of the above sources. One potential mechanism involves the deacetylation of chitin in excess sodium hydroxide (aq).

In one embodiment, the modified polymer is obtained by contacting a polymer selected from the group of polysaccharides and lignin, with an organic phosphonate compound to give a modified polymer, In another embodiment, the modified polymer may be obtained by contacting a polymer matrix (e.g. pulverized wood or arthropod shells) with an organic phosphonate compound, followed by filtration to yield a modified polymer. For example, wood or arthropod shells may be co-extracted and modified during the same treatment.

The resulting modified polymer is, depending on the degree of reaction (i.e. "degree of substitution" of phosphonate groups), soluble or partially soluble in solvents, such as water and aqueous solutions, for example aqueous solutions formed from water and polar solvents, such as any of the above mentioned aliphatic or aromatic alcohol. At lower substitution degree of phosphonate groups, the polymer may form gels in the above solvents.

The modified polymer can be separately recovered from the solution, or the solution or gel can be used as such. The polymers can be converted to fibres or films.

Figure 4:
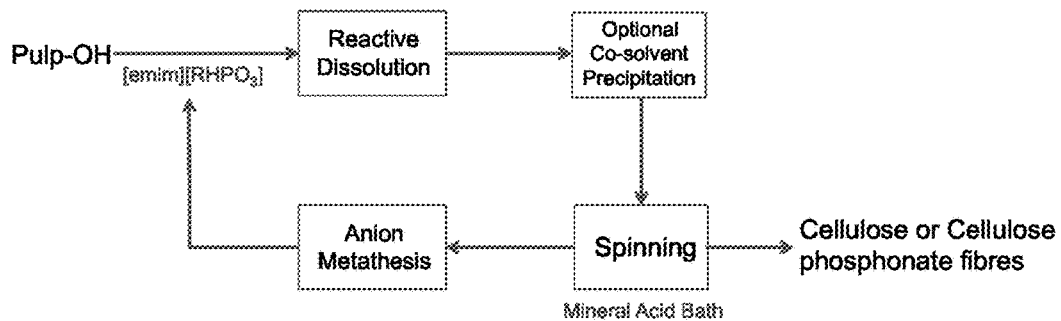
FIG. 4 shows a potential process diagram for pulp modification and spinning into acid solution to yield phosphonate-functionalised cellulose fibres, which can be partially functionalised by phosphonate groups.

FIG. 4 is a process diagram illustrating a process for pulp modification and spinning into acid solution to yield cellulose fibres or phosphonate functionalized fibres.

As can be seen, the cation, in this case, 1-ethyl-3-methylimidazolium, is recovered after dilute wash of the phosphonylated polymer with a mineral acid, such as sulphuric acid.

The cation is circulated and anion metathesis is carried out e.g. by anion exchange or electrodialysis. Thus the phosphonate salt is formed (dope, 1-ethyl-3-methylimidazolium methylphosphonate, abbreviated [emim][MeHPO$_3$]). The washed phosphonylated polymer can be recovered separately and used for further processing.

Figure 5:
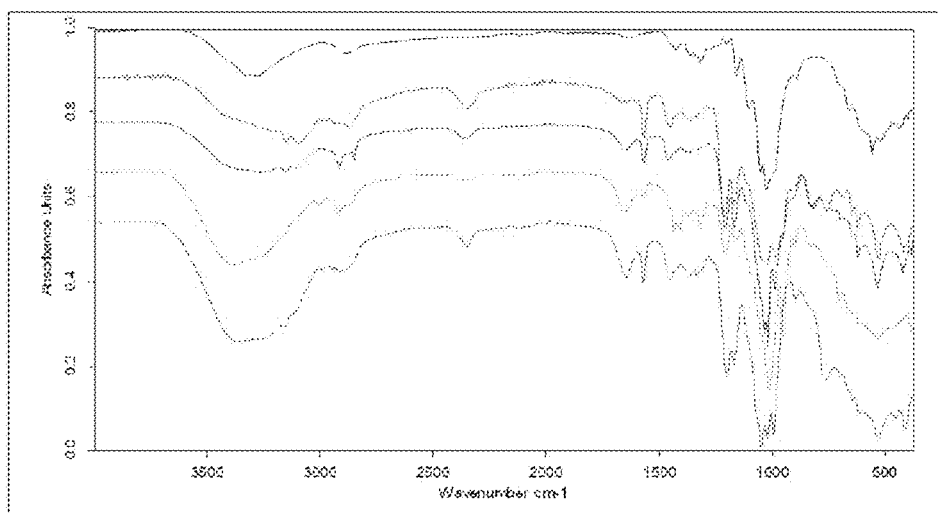
FIG. 5 shows IR spectra with stretches corresponding to cellulose functionalised with phosphonate groups, under various reaction conditions. Phosphonate peak is observed at 2360 cm$^{-1}$.

The original polymer can also be regenerated from the modified polymer, as evidenced by Example 6 and FIG. 5. Thus, regeneration can be performed by acidification of a solution, for example an aqueous solution, of the polymer.

In one embodiment the polymer is provided in the form of fibres or filaments.

Spun fibres comprising the polymer are disclosed in an additional embodiment. In a further embodiment a thin film comprising the polymer is described. In a particular embodiment the thin film exhibits the properties of an oxygen barrier. The films have been demonstrated to be excellent oxygen barriers that are flexible, transparent and do not tear easily. These properties make the thin films particularly suitable for use in the food packaging industry.

Yet further embodiments provide polymer solutions comprising a concentration of polymer. In one embodiment a polymer solution comprises the polymer dissolved or dispersed in a liquid phase. In a further embodiment the liquid phase comprises a polar solvent, such as water or aqueous solutions. In a particular embodiment the concentration of the polymer in the liquid phase is 0.1 to 20% by weight of the polymer solution, calculated from the total weight of the solution.

The following non-limiting examples illustrate embodiments of the present technology.

EXAMPLES

Example 1

1-Ethyl-3-Methylimidazolium Methylphosphonate ([emim][MeHPO$_3$]) Synthesis

1-Ethylimidazole (96.1 g, 1.00 mol) was added dropwise (over 1 h) to neat dimethylphosphite (110.0 g, 1.00 mol) at 85° C. The reaction was allowed to stir for a further 18 h at 80° C. The mixture was rotary evaporated at 65° C. under high vacuum for 18 h, to yield a clear pale yellow oil (206.0 g).

The reactants and the reaction steps are also shown in FIG. 1.

Example 2

Methyltrioctylphosphonium Methylphosphonate ([P$_{8881}$][MeHPO$_3$]) Synthesis

Trioctylphosphine (370 g, 1.00 mol) was added dropwise (over 1 h) to neat dimethylphosphite (110.0 g, 1.00 mol) at 85° C. under argon. The reaction was allowed to stir for a further 18 h at 80° C. The mixture was rotary evaporated at 65° C. under high vacuum for 18 h, to yield a clear pale yellow oil (480 g).

Example 3

Modification of Pre-Hydrolysis Kraft (PHK) Pulp with [emim][MeHPO$_3$] at 130° C.

[emim][MeHPO$_3$] 95 g was added to a flask containing PHK (5 g). The mixture was stirred under argon atmosphere for 18 hr at 130° C. The reaction mixture was diluted with an equal volume of methanol and filtered through a G3 sintered funnel. The crude product was precipitated by a slow addition of acetone (3 volumes). The precipitates were washed with further acetone:methanol (95:5). The material was reprecitated again using the same methanol acetone precipitation and volumes. The resulting sample was then dried in a vacuum oven to yield a white powder (9.5 g). The resulting product was water soluble.

Figure 2:
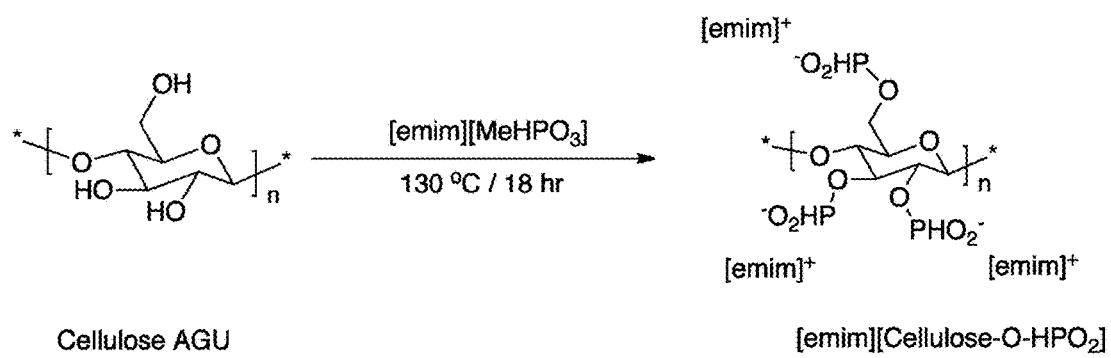
FIG. 2 shows a potential reaction mechanism for the synthesis of cellulose phosphonate.
Figure 3:
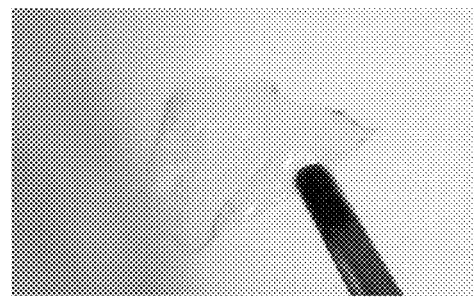
FIG. 3 shows a thin film of transparent and flexible cellulose phosphonate, cast from aqueous solution.

The reactants and the reaction steps are also shown in FIG. 2.

Example 4

Modification of Pre-Hydrolysis Kraft (PHK) Pulp with [emim][MeHPO$_3$] at 100° C. Using DBU as catalyst

[emim][MeHPO$_3$] 95 g was added to a flask containing PHK (5 g). DBU (100 mg) was added. The mixture was stirred under argon atmosphere for 18 hr at 100° C. The reaction mixture was diluted with an equal volume of methanol and filtered through a G3 sintered funnel. The crude product was precipitated by a slow addition of acetone (3 volumes). The precipitates were washed with further acetone:methanol (95:5). The material was precipitated again using the same methanol acetone precipitation and volumes. The resulting sample was then dried in a vacuum oven to yield a white powder (8 g). The product formed a gel in water.

Example 5

Modification of Chitosan with [emim][MeHPO$_3$] at 130° C.

[emim][MeHPO$_3$] 95 g was added to a flask containing chitosan (5 g). The mixture was stirred under argon atmosphere for 18 hr at 100° C. The reaction mixture was precipitated with acetone:methanol (95:5). The mixture was heated with DMA at 60° C. for 18 hr. The resulting sample was then dried in a vacuum oven to yield an amber powder (9.5 g).

Example 6

Regeneration of Cellulose from Cellulose Phosphonate

Cellulose phosphonate (0.25 g) was dissolved in water (5 ml). This solution was then added into 1M HCl (5 ml) and stirred at RT for 1 hr. A white solid precipitated over this period. This was filtered off and washed with water. This was dried and analysed by IR.

The material showed IR stretches corresponding to cellulose but none to phosphonate or [emim] cation (FIG. 5).

The present technology is suitable for use in the pulp industry, for preparation of low and high-value functional polymers. The present simple, easy to conduct method of polymer modification under moderate conditions provides novel polymers that can be used in a variety of applications ranging from packaging to the automotive industry where the novel polymers can be used in the production of mouldable plastics to be used in both moving and non-moving parts and in the textile industry where the novel polymers can be used for the production of new textiles that can be breathable and/or waterproof. The polymers are also suitable for use in the production of body armour.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A method of modifying a polymer having hydroxyl groups to obtain a modified polymer, comprising the step of contacting said polymer with at least one organic phosphonate salt in order to chemically modify the polymer, said at least one organic phosphonate salt being in the liquid phase, and wherein the at least one organic phosphonate salt is of Formula III

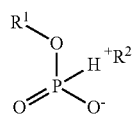

III wherein
R$^1$ is selected from a hydrogen radical, a linear or branched alkyl radical having 1 to 20 carbon atoms, an aryl radical having 4 to 24 carbon atoms, and R$^2$ is a cation selected from the group of substituted and unsubstituted phosphonium, substituted and unsubstituted sulfonium, and mixtures thereof.

2. The method according to claim 1 wherein R$^1$ is an aryl radical comprising at least one heteroatom selected from O, N and S.

3. The method according to claim 1 wherein R$^1$ is an alkyl or aryl radical substituted with 1 to 10 substituents selected from hydroxyl, carboxy, halo, amino, and thio groups.

4. The method according to claim 1, wherein the modified polymer contains unreacted hydroxyl groups.

5. The method according to claim 4, wherein the ratio of phosphonate groups to hydroxyl groups in the modified polymer is 1000:1 to 1:1000.

6. The method according to claim 4, wherein the ratio of phosphonate groups to hydroxyl groups in the modified polymer is 100:1 to 1:100.

7. The method according to claim 4, wherein the ratio of phosphonate groups to hydroxyl groups in the modified polymer is 10:1 to 1:10.

8. The method according to claim 1, wherein the amount of the at least one organic phosphonate salt in the liquid phase is between 0.1 and 100.0% of the total weight of the liquid phase.

9. The method according to claim 1, wherein the amount of the at least one organic phosphonate salt in the liquid phase is between 1.0 and 50.0%, of the total weight of the liquid phase.

10. The method according to claim 1, wherein the amount of the at least one organic phosphonate salt in the liquid phase is between 2.0 and 20.0% of the total weight of the liquid phase.

11. The method according to claim 1, wherein the amount of the at least one organic phosphonate salt in the liquid phase is between 8.0 and 12.0%, of the total weight of the liquid phase.

12. The method according to claim 1, wherein the polymer is contacted with the at least one phosphonate salt at a molar ratio of hydroxyl groups to phosphonate groups of 1:0.1 to 1:1000.

13. The method according to claim 1, wherein the polymer is contacted with the at least one phosphonate salt at a molar ratio of hydroxyl groups to phosphonate groups of 1:0.5 to 1:100.

14. The method according to claim 1, wherein the polymer is contacted with the at least one phosphonate salt at a molar ratio of hydroxyl groups to phosphonate groups of 1:1 to 1:50.

15. The method according to claim 1, wherein the polymer is modified by chemical reaction between the at least one organic phosphonate salts and hydroxyl groups of the polymer, said chemical reaction giving polymer phosphonates and a weight percent gain (WPG) in the polymer of 0.001-60.000%.

16. The method according to claim 1, wherein the polymer is modified by chemical reaction between the at least one organic phosphonate salt and hydroxyl groups of the polymer, said chemical reaction giving polymer phosphonates and a weight percent gain (WPG) in the polymer of 1.000-55.000%.

17. The method according to claim 1, wherein the polymer is modified by chemical reaction between the at least one organic phosphonate salt and hydroxyl groups of the polymer, said chemical reaction giving polymer phosphonates and a weight percent gain (WPG) in the polymer of 5.000-50.000.

18. The method according to claim 1, wherein the polymer is modified by chemical reaction between the at least one organic phosphonate salt and hydroxyl groups of the polymer, said chemical reaction giving polymer phosphonates and a weight percent gain (WPG) in the polymer of 10.000-40.000%.

19. The method according to claim 1, wherein the polymer is selected from polysaccharides and lignin.

20. The method according to claim 1, wherein R$^2$ is a phosphonium ion substituted by one or more groups selected from the group of linear or branched alkyl radicals, said alkyl radicals having 1-10 carbon atoms, and aryl radicals having 4-24 carbon atoms, optionally comprising at least one heteroatom selected form O, N, and S, said alkyl and said aryl radical being optionally substituted with 1 to 10 substituents selected from hydroxyl, carbonyl, halo, amino, and thio groups.

21. The method according to claim 20, wherein R$^2$ is methyltrioctylphosphonium.

* * * * *

UNITED STATES PATENT AND TRADEMARK OFFICE
CERTIFICATE OF CORRECTION

PATENT NO. : 10,208,132 B2
APPLICATION NO. : 14/893751
DATED : February 19, 2019
INVENTOR(S) : Alistair W. T. King et al.

It is certified that error appears in the above-identified patent and that said Letters Patent is hereby corrected as shown below:

In the Claims

Column 10 in Claim 17, Line 42, should correctly appear as --5.000-50.000%.--

Signed and Sealed this
Fourteenth Day of May, 2019

Andrei Iancu
*Director of the United States Patent and Trademark Office*